(12) United States Patent
Adams

(10) Patent No.: US 9,545,395 B2
(45) Date of Patent: Jan. 17, 2017

(54) METHOD AND COMPOSITION FOR ENHANCEMENT OF MALE ERECTILE FUNCTION

(76) Inventor: Kenneth W. Adams, North York (CA)

( * ) Notice: Subject to any disclaimer, the term of this patent is extended or adjusted under 35 U.S.C. 154(b) by 0 days.

(21) Appl. No.: 13/127,889

(22) PCT Filed: Nov. 5, 2009

(86) PCT No.: PCT/CA2009/001591
§ 371 (c)(1),
(2), (4) Date: Jul. 5, 2011

(87) PCT Pub. No.: WO2010/051631
PCT Pub. Date: May 14, 2010

(65) Prior Publication Data
US 2011/0263498 A1    Oct. 27, 2011

(30) Foreign Application Priority Data

Nov. 6, 2008 (CA) .................... 2643529

(51) Int. Cl.
| | | |
|---|---|---|
| A61K 38/30 | (2006.01) | |
| A61K 31/417 | (2006.01) | |
| A61K 31/46 | (2006.01) | |
| A61K 31/472 | (2006.01) | |
| A61K 31/5415 | (2006.01) | |
| A61K 31/5578 | (2006.01) | |
| A61K 31/568 | (2006.01) | |

(52) U.S. Cl.
CPC ............. *A61K 31/417* (2013.01); *A61K 31/46* (2013.01); *A61K 31/472* (2013.01); *A61K 31/5415* (2013.01); *A61K 31/5578* (2013.01); *A61K 31/568* (2013.01); *A61K 38/30* (2013.01)

(58) Field of Classification Search
None
See application file for complete search history.

(56) References Cited

U.S. PATENT DOCUMENTS

| 5,916,569 A | * | 6/1999 | Spencer et al. | ............ 424/198.1 |
| 7,258,864 B2 | * | 8/2007 | Clark | ......................... 424/198.1 |
| 2011/0009318 A1 | * | 1/2011 | White et al. | .................. 514/8.6 |

FOREIGN PATENT DOCUMENTS

WO    WO 2005/011705    *    2/2005

OTHER PUBLICATIONS

Bochinski et al., International Journal of Impotence Research, 16:418-423, 2004.*
Abdelbaky et al. Endocrinology, 139:3143-3147, 1998.*
Pu, Insulin-like Growth factor-1 restores erectile function in aged rats: Modulation of the integrity of smooth muscle and nitric oxide-cyclic guanosine monophosphate signaling activity, J Sexual Medicine, Jun. 2008, vol. 5, No. 6, p. 1345-1354.
Guay, Testosterone and erectile physiology, The Aging Male, Dec. 2006, vol. 9, No. 4, p. 201-206.
Iribarren, Pharmacological treatment of erectile dysfunction, Current Opinion in Urology, Nov. 1999, vol. 9, No. 6, p. 547-551.

* cited by examiner

*Primary Examiner* — Marianne P Allen
(74) *Attorney, Agent, or Firm* — Jeffrey S. Melcher; Manelli Selter PLLC

(57) ABSTRACT

A pharmaceutical composition for enhancing male erectile function comprising an erectile function-enhancing amount of an insulin-like growth factor selected from the group consisting of IGF-1 (Somatmedin-C) and analog LR3 IGF1 in admixture with a pharmaceutically-acceptable diluents or carrier. Such compositions optionally further comprise compounds selected from an androgen, particularly, testosterone and dihydrotestosterone, a vasodilator, PDE5 inhibitor and prostaglandin E1.

8 Claims, No Drawings

METHOD AND COMPOSITION FOR ENHANCEMENT OF MALE ERECTILE FUNCTION

CROSS-REFERENCE TO RELATED APPLICATIONS

This application is a national stage entry under 35 U.S.C. 371 of International Application No. PCT/CA2009/001591, filed 5 Nov. 2009, designating the United States. This application claims foreign priority under 35 U.S.C. 119 and 365 to Canadian Patent Application No. 2,643,529, filed 6 Nov. 2008.

FIELD OF THE INVENTION

The invention relates to methods and compositions for enhancing male erectile function, particularly using Somatomedins insulin-like growth factors.

BACKGROUND OF THE INVENTION

Erectile dysfunction (ED) is defined as the inability to achieve and maintain a penile erection adequate for sexual intercourse. This may be a relative term wherein the frequency of occurrences in which a patient is able to achieve and maintain a penile erection adequate for sexual intercourse has decreased over time as a part of natural aging which is superimposed with other internal and external factors that impact negatively upon the natural sexual responses of males. It is a male health problem which in its most severe form has been estimated to affect about 150 million men worldwide. But in North America it is estimated that by the age of 40 years, approximately 25% of men are having problems with achieving and sustaining an erection, and this probably increases to over 50% for men over 60 years of age.

Impotence generally refers to a severe form of male erectile dysfunction and is defined as the general inability to achieve and sustain an erection sufficient for intercourse. Erectile function naturally declines with age and like the aging process, the decline in erectile function experienced by men as they age is a complex biological phenomena that results from complicated interactions between psychological, emotional, spiritual and physical factors. Some of the physical factors include genetics, diet, nutrition, environmental exposures to toxins, radiation, hormonal factors such as thyroid, adrenal, gonadal, and growth hormones among others: as well as effects from medications and other iatrogenic effects of medical treatments. These are only some of the various factors that may contribute to natural diseases that combine with aging to cause declining sexual function in men and women.

The complexity of the body makes the diagnosis and treatment of ED imprecise. The hormonal issues are rarely considered in diagnostic workups. For example, the assessment of thyroid, adrenal and growth hormones are not part of the usual diagnostic workup. Even though physicians and the medical literature are now starting to acknowledge testosterone in practical terms, it is rarely considered when a man is being treated for erectile dysfunction. Even though disturbances in these hormonal systems will significantly impact erectile function, they are generally ignored when erectile dysfunction is assessed and treated. In summary, the understanding of erectile dysfunction is very imprecise in modern medical practice.

There is currently no standardized method of diagnosis or treatment that begins to address the many normal causes of ED. The diagnosis of erectile dysfunction generally relies on self-reporting by patients. Since the majority of men experiencing significant erectile dysfunction will not be aware that they are having erectile dysfunction they will not report any concerns to their physician. Even when they are given medical therapies that worsen their erectile function, for example, many common prescription medications, such as anti-hypertensives will worsen erectile function while other medications may improve their erectile function, they will be unaware of these changes. It is the experience of the inventor that patients and physicians tend to recognize only more profound levels of erectile dysfunction and most cases of declining or improving erectile function go unrecognized.

Histologically there are specific changes that have been well documented in the penis of men with erectile dysfunction that tend to increase with age. Men who experience declining erectile function have actual physical changes within their penis. Some of these changes include reduced smooth muscle, reduced diameter and size of the cavernosal nerves, reduced levels of elastin and increased levels of collagen all of which result in impaired vascular response, reduced relaxation of the cavernosal sinuses and impairment of the veno-occlusive mechanism to properly pressurize the cavernosal system. None of the current therapies for erectile function address or are known to treat or improve these physical changes.

All of the current medications being used to treat erectile dysfunction work by directly or indirectly causing smooth muscle relaxation in the erectile tissue. This results in dilation of the arteries bringing blood into the erectile tissue and dilation of the cavernosal sinuses. These effects are transient, from minutes to several hours and they can only be effective while they are present in the penis at therapeutic levels, and this would include oral agents (phosphodiesterase-5 inhibitors, such as Levitra™, Viagra™, and Cialis™, dopamine agonists, such as Uprima™, and alpha-receptor blocking drugs), intracavernosally injected vasodilators (papaverine, phentolamine, prostaglandin E1, vasoactive intestinal peptide), transurethral vasoactive agents (prostaglandin E1, sometimes marketed as MUSE™), vacuum erection devices, and vascular surgery. Rings work by reducing venous out flow relative to inflow. Penile prostheses simply replace the erectile tissue with a rigid or semi-rigid structure. Each of these options has its own disadvantages. However, all of the current medications do not reverse or improve the physical changes causing erectile dysfunction, hence, they have no ability to cure erectile dysfunction. They can be effective while these medications are present at therapeutic levels in the tissues where they directly exert their effects.

Current pharmacological treatments for erectile function such as phosphodiesterase 5-blockers and intracavernosally administered medications, such as the vasodilator PGE1alpha improve erectile responses by transiently producing elevated levels of blood flow and increased dilation of the cavernosal tissue to allow the arterial inflow to sufficiently pressurize the erectile tissue and activate the veno-occlusive system tissue to produce a usable erection.

It is known that men who consistently under all circumstances fail to respond with functional erections to maximal pharmacotherapy with oral or intracavernosal medications have to resort to using a pump and a very tight penile ring or undergo the surgical insertion of an implant. Frequent prolonged use of pumps and rings will damage the penis, and surgery results in an immediate irreversible destruction of the erectile tissues.

Histologically, there are specific changes that are associated with erectile dysfunction. These histological changes are:
1. increase in the percentage of collagen relative to smooth muscle in the cavernosal tissues;
2. decrease in the percentage of smooth muscle relative to collagen in the cavernosal tissues;
3. reduced elastin;
4. decreased cavernosal arterial inflow;
5. decreased cavernosal expansion during sexual stimulation; and
6. increased level of sexual stimulation needed to achieve and maintain a functional erection.

There is, therefore, a need for a safe, effective treatment that would induce long lasting physical changes in the penis that would allow a man's penis to be functional without the need to take a pill or inject medication into the penis every time he wants to be sexually active, and that could actually induce long lasting physical changes in the penis that would improve erectile function after medication had been discontinued.

SUMMARY OF THE INVENTION

The inventor has discovered that the local application of low doses of hormones of use according to the invention at 10 to 4000 times less than the systemic doses that would be used to treat medical conditions unrelated to erectile dysfunction can effectively treat erectile dysfunction and induce physical changes to improve erectile function.

Somatomedin-c (IGF1, Mecasermin, CEP-151, FK-780, Insulin-like growth factor 1, rhIGF1, Mescarina, Mescarmine, Mescarmina Rinfabate) or lr IGF1 or Long IGF1-lr3 or any other functional agonist of the IGF1 receptor (or its functional equivalent) herein termed "SC", is an Insulin like Growth factor that is stimulated to be produced mainly in the liver and other sites in the body that can respond to Human Growth Hormone. In the practise of the present invention, it has been used at doses starting doses of 40-80 µg/kg twice daily which would be 6,000 to 12,000 µg/day or 42,000 to 84,000 for a 75 kg male, and to a maximum of 120 µg/kg twice daily which would be 18,000 µg/day or 126,000 µg/week.

The inventor has found that men injecting Somatomedin-C in doses as low as 50-100 µg/once per week into a single or multiple sites sub-cutaneously or even subdermally in the penis obtained a dramatic improvement in their erectile function. A dose of 50 µg per week is 1/2500 of the recommended maximum systemic dose for a 75 kg male. Alternatively, men who were regularly using intracavernosal injections to function sexually could just add 10-50 µg of IGF1 to their routine intracavernosal injections.

Further, the inventor has found that men who were locally injecting 6-12 units/week of long IGF1-lr3 (also called lr-IGF1 by some manufacturers) seemed to be roughly equivalent to the Somatomedin-C dose of 50-100 µg/once per week into a single or multiple sites sub-cutaneously or even subdermally in the penis had a dramatic improvement in their erectile function. Alternatively, men who were regularly using intracavernosal injections could inject IGF-1 alone or alternatively add a dose of 2-6 µg of long IGF1-lr3 into their usual dose of intracavernosal medication to reduce the number of injections into the penis. A dose of 2-6 µg of long IGF1-lr3 seemed to be equivalent to 10-50 µg Somatomedin-C (IGF1) dose being premixed or simply added at the time the syringe was loaded from a multi-dose sterile bottle to their routine intracavernosal injections.

Even local subdermal, subcutaneous or deeper injections at doses of IGF1-lr3 as low as 0.5-2 µg applied daily or 5-20 µg applied weekly, or equivalent dose or other IGF1 receptor agonist, gave a clinical response. Men who had used the higher locally applied penile doses listed above and who relied on PDE5's to treat their ED started to get functional erections without the need for PDE5's within 1-2 weeks and the improvement in erectile function continued beyond 6 weeks. In fact, the longer they used this IGF1 treatment the easier it became to achieve a spontaneous erection without any medication. The longer they used the treatment, the longer the effects lasted upon discontinuation. Men who had used only a couple of doses of IGF1 found the functional improvement that occurred noticeably started weakening after 1-2 weeks and was essentially gone after a month. However, men who had used the treatment for longer periods noticeably took longer before they felt their erectile function was declining, and some men found the benefits of this treatment lingered for several months after the treatment stopped.

It should be noted that higher doses injected at the frequencies listed above were more effective. The effectiveness of these therapies can be increased with lower doses applied more frequently to the penis, although the use of multiple injections may not be tolerated as well. For comfort, the finest commercially available needles are preferred, such as, for example, 30 or 31 gauge. Further, a small implantable form of mechanical device or pellet planted under the skin or other externally applied device to produce a sustained slow continuous or pulsed release of a biologically active of IGF1 receptor agonist with or without androgen also tended to improve bioavailability while reducing the total dose of these hormones that are delivered to the tissues of the penis.

When IGF's such as IGF-1 (Somatomedin-C) and analogue LR3 IGF1, androgens, vasodilators, or type 5 phosphodiesterase inhibitors are locally applied, they cannot exert any physiological effect on distant tissues until they have been transported to these distant tissues. The process dispersion and transportation will result in concentrations in these distant sites that are multiple magnitudes of order lower than the levels present originally in the penis.

The positive effects of the IGF-1 receptor agonists, e.g. IGF-1 (Somatomedin-C; analogue LR3 IGF1) when combined with androgens on erectile function have also been observed by the inventor to be almost entirely local. The inventor discovered that when small systemic doses of IGF's or IGF's and androgens are applied to a male that have no detectable response when applied systemically, i.e. doses that would be too low to raise the systemic levels or physiologic levels of these hormones in the serum when administered systemically, the same dose when applied locally to the penis and genital structures causes a dramatic improvement in erectile function. For example, doses of IGF1 receptor agonist and androgens that are 1/10 to 1/2500 of the minimum systemic dose necessary for a male to report an improvement in their erectile function, when this same dose of IGF's or IGF's and androgen are applied locally to the penis, they have a dramatically stronger effect than the much larger systemic dose applied systemically. A male will observe dramatically harder and firmer erection when stimulated. On the contrary, if these locally effective doses of 1/10-1/2500 of an effective systemic dose are then applied systemically outside the penis, the positive benefits observed from local an application will disappear.

In a preferred aspect, IGF's and androgens are applied locally at very low doses to yield optimal erectile function due to their local action in the penis while minimizing side-effects.

As a result of the small volume of the penis relative to the rest of the body, small systemic doses have profound effects when applied directly to the penis. This is accompanied by dramatically lower systemic levels and significantly lower risks of systemic side effects. Effective local application of low dose IGF-1 receptor agonists will eliminate or significantly diminish the known side effects of long term administration of IGF1 receptor agonist such as organomegaly, enlargement of hands, feet and other hard and soft tissues of the body. As stated hereinabove, generally, doses 1/500 to 1/2500 of the systemic dose can be applied locally for good effect.

It is possible to locally apply to the penis doses greater than 1/10 of the systemic dose, but these higher doses would (1) produce tissue levels in the penis where the dose response curve was flat and where high concentrations would yield minimal benefit due to saturation of receptors; (2) cause physiologic or supra-physiologic levels outside of the penis which would also be beneficial but these higher levels would clearly be associated with much higher risks of negative or unwanted side effects both locally in the penis and systemically.

Conversely doses below 1/2500 of the systemic dose will also be beneficial, but the positive effects are not as robust and much more subtle to detect clinically.

Clearly, even if local doses were applied systemically, which would generally be 1/500 to 1/2500 of the maximal safe systemic dose are administered systemically of IGF's (IGF-1 (Somatomedin-C) and analogue LR3 IGF1) alone, of IGF's (IGF-1 (Somatomedin-C) and analogue LR3 IGF1) and androgens, IGF's (IGF-1 (Somatomedin-C) and analogue LR3 IGF1) in combination with locally applied vasodilators, of IGF's (IGF-1 (Somatomedin-C) and analogue LR3 IGF1) combined with PDE's, and with IGF's (IGF-1 (Somatomedin-C) and analogue LR3 IGF1) and androgens combined with vasodilators or PDE's, it will be difficult to clinically observe a clear beneficial effects on erectile function. Once again, when a small systemic dose is applied outside the penis, it will be diluted thousands of times as it disperses systemically before it can be transported by the circulatory system to the penis, compared to the high tissue levels achieved by a local application into the penis.

To be effective, systemic applications require dramatically larger doses, and the risks of toxicity and safety will limit the beneficial effects of systemic applications of these medications (IGF's, androgens, vasodilators, phosphodiesterase inhibitors) relative to the lower local doses recommended in this invention. In most cases it has been discovered by the inventor that the largest safe systemic doses cannot achieve the same benefit to erectile function on the penis as a much smaller and much safer locally applied dose of these medications.

In one aspect, the invention provides a pharmaceutical composition for enhancing male erectile function comprising an erectile function—enhancing amount of an insulin-like growth factor 1 agonist selected from the group consisting of IGF-1 (Somatomedin-C) and analogue LR3 IGF1 in admixture with a pharmaceutically-acceptable diluent or carrier.

In a further aspect, the invention provides a method of enhancing male erectile function comprising administering to a male a composition comprising an erectile function-enhancing amount of an insulin-line growth factor selected from the group consisting of IGF-1 (Somatomedin-C) and analogue LR3 IGF1 in admixture with a pharmaceutically-acceptable diluent or carrier.

In a further aspect, the invention provides a use of a composition comprising an effective amount of insulin-like growth factor selected from the group consisting of IGF-1 (Somatomedin-C) and analogue LR3 IGF1 and a pharmaceutically-acceptable carrier or diluents for enhancing male erectile function.

In a further aspect, the invention provides a method of manufacturing a medicament intended for the application of enhancing male erectile function characterized in that insulin-like growth factor (IGF) selected from IGF-1 (Somatomedin-C) and LR3 IGF1 is admixed with a pharmaceutically-acceptable carrier.

The present invention provides for methods, compositions, uses and kits for the enhancement of male erectile function, which involves the administration of an insulin-like growth factor.

Preferably, the IGF is Somatomedin-c (IGF1, Mecasermin, CEP-151, FK-780, Insulin-like growth factor 1, rhIGF1, Mescarina, Mescarmine, Mescarmina Rinfabate) or lr IGF1 or Long IGF1-lr3 or any other functional agonist of the IGF1 receptor (or its functional equivalent).

IGF-1 (Somatomedin-C) comprises a full length protein of 70 amino acids in a single chain with three intramolecular disulfide bridges. Examples of recombinant human IGF-1 and recombinant LR3 IGF-1 are products made by GroPep Ltd. (Adelaide, Australia) and other commercial laboratories.

Preferably, the invention provides a use as hereinabove defined wherein said composition further comprises an androgen.

Preferred androgens to be combined with an insulin-like growth factor 1 receptor agonist are selected from testosterone, or dihydrotestosterone, or testosterone and dihydrotestosterone or pharmaceutically-acceptable esters of testosterone and dihydrotestosterone, pharmaceutically-acceptable derivatives of testosterone such as methyl testosterone, testolactone, oxymetholone and fluoxymesterone. Testosterone and testosterone esters, such as testosterone enanthate, testosterone propionate and testosterone cypionate, may be used. The aforementioned testosterone esters are commercially available or may be readily prepared using techniques known to those skilled in the art or described in the pertinent literature.

In a further use as hereinabove defined the compositions of LR3 IGF-1 or IGF1 further comprise a vasodilator. Preferably, the vasodilator is selected from the group consisting of papaverine, chlorpromazine, atropine, phentolamine, a prostoglandin and mixtures thereof.

In a further use as hereinabove defined the compositions of LR3 IGF-1 or IGF1 further comprises an androgen and a vasodilator.

Preferably, in further embodiments the compositions further comprise a prostaglandin, preferably prostaglandin E1.

Preferably, use of the compositions in the practice of the invention comprises applying the composition locally to the penis intracavernosally at a dose selected from 0.1 to 100 μg.

Preferably, the male is a man.

In a preferred practice of the invention, the IGF-1 compositions of LR3 IGF-1 or IGF1 of use according to the invention are administered, for example, by subcutaneous injection, high pressure jet device, intracavernous injection, intravenous injection, small implantable mechanical device, small pellet, externally applied pump and syringe, intramuscular injection, intradermal injection, intra-nasal or topical administration while the vasodilator is delivered only by intracavernosal injection.

The male erectile dysfunction to be treated or prevented is, most generally, erectile dysfunction from all causes, both primary and induced by known and unknown secondary causes of erectile dysfunction such as hereinbefore described including but not limited to hormonal imbalances, nutritional imbalance, pharmaceutically induced, prolonged stress and psychological causes, to nerve dysfunction, arterial insufficiency, venous leakage, severe vascular insufficiency, mild vascular disease, hormonal insufficiency, drug use, surgery, chemotherapy, or radiation.

Small locally applied doses of IGF-1 (Somatomedin-C) and analogue LR3 IGF1 which produce low systemic doses will in turn eliminate or reduce and systemic effects and systemic side effects while producing very significant improvement in erectile function. For example, a male may have to take 50-150 mcg of IGF-1 (Somatomedin-C) or analogue LR3 IGF1 on a daily basis systemically to effect the same improvement in erectile function as 2-5 mg of IGF-1 (Somatomedin-C) or analogue LR3 IGF1 applied locally to the penis. And if the same male applied 2-5 mcg of IGF-1 (Somatomedin-C) or analogue LR3 IGF1 systemically at a site outside of the genital area he would observe no improvement in his erectile function.

In a further aspect, the IGF-1 composition comprising LR3 IGF-1 or IGF1 is administered locally to the penis in combination with preferably an androgen such as testosterone and dihydrotestosterone administered by subcutaneous injection, high pressure jet device, intracavernosal injection, intravenous injection, intramuscular injection, intradermal injection, intra-nasal or topical administration, internal micropump or slow release technology, or external pump.

In a further aspect, the invention provides use of a composition for the manufacture of a medicament for treating male erectile dysfunction in a mammal characterized in that said composition comprises an insulin-like growth factor (Somatomedin-c (IGF1, Mecasermin, CEP-151, FK-780, Insulin-like growth factor 1, rhIGF1, Mescarina, Mescarmine, Mescarmina Rinfabate) or lr IGF1 or Long IGF1-lr3 or any other functional agonist of the IGF1 receptor (or its functional equivalent) as hereinbefore defined.

In a preferred aspect, the invention provides a use as hereinabove defined wherein said IGF is LR3 IGF-1, or IGF-1 (Somatomedin-C).

In a further aspect, the invention provides a use as hereinabove defined wherein said composition further comprises an androgen injected with androgen.

In a further aspect, the invention provides a use as hereinabove defined wherein said composition for the injectable mixture further comprises a vasodilator.

In a further aspect, the invention provides a use as hereinabove defined wherein said composition further comprises an androgen and a vasodilator.

In a further aspect, the invention provides a use as hereinabove defined wherein said composition further comprises a PDE5 inhibitor.

In a further aspect, the invention provides a use as hereinabove defined wherein said composition further comprises an androgen and a PDE5 inhibitor.

In a further aspect, the invention provides a use as hereinabove defined wherein said composition further comprises an androgen, PDE5 inhibitor and a vasodilator.

In a further aspect, the invention provides a use as hereinabove defined wherein said composition further comprises a prostaglandin.

In a further aspect, the invention provides a method for manufacturing a medicament intended for the application of treating male erectile dysfunction characterized in that insulin-like growth factor (IGF-1 Somatomedin-c (IGF1, Mecasermin, CEP-151, FK-780, Insulin-like growth factor 1, rhIGF1, Mescarina, Mescarmine, Mescarmina Rinfabate) or lr IGF1 or Long IGF1-lr3 or any other functional agonist of the IGF1 receptor (or its functional equivalent) is admixed with a pharmaceutically-acceptable carrier.

In a further aspect, the invention provides for a kit comprising the above-described combinations and an instruction for using the combination in treating, improving, curing or preventing male erectile dysfunction.

As used herein, "enhanced erectile function" refers to the ability to achieve and maintain a penile erection adequate for sexual intercourse more often than the man was able to before the treatment presented in the instant application. Indications that this treatment is effective include the decreased or eliminated reliance on medications and/or improved response to the medications currently used to treat erectile dysfunction or aid in achieving an adequate erection, more frequent spontaneous erections, an improved ability to sustain an erection before and after ejaculation, a reduction in the absolute and relative refractory period after ejaculation before another erection can be achieved, a reduced requirement for stimulation to achieve and maintain an erection and an increase in frequency, firmness and duration of morning erections and an increase in frequency, firmness and duration of spontaneous erections. Any of these indicators, alone or in combination, can be used as a measure of effectiveness.

Administration to the cavernosal tissue encompasses injections directly into the cavernosal tissue, which is preferred for men who have previously been trained on the proper method for intracavernosal injections and are currently using intracavernosal injections. For men who are not skilled with IC injections, the preferred injection would be injections to the connective tissues, which surround the cavernosal tissue from where the active agents of the present invention, in a water-based or oil-based system, will diffuse into the cavernosal tissue. Through this route, generally less of the administered dose would be delivered to the cavernosal tissue than if it were injected directly into the cavernosal tissue. Other routes of administration considered to be administration to the cavernosal tissue include urethral suppositories, implantable sustained-release drugs or devices, and transdermal devices or vehicles which are directly in contact with or adhered to the penis, such as patches, creams, or lotions. Optionally, the transdermal devices or vehicles may be delivered by a condom-like device.

In preferred embodiments of the invention the pharmaceutical compositions are administered to the penile and cavernosal tissue of the penis of a male patient.

The pharmaceutical composition is administered to the patient in a pharmaceutically acceptable sterile dosage form to the tissues of the penis, which includes the cavernosal tissue. The composition may be administered topically by transdermal vehicles or devices, such as creams, lotions, or patches. The composition may be administered by urethral suppository, or parenterally using a needle, auto-injector, slow sustained injection pump, high pressure jet injection device, microinfusion pump, or implantable sustained release drug or device. Sterile dosage forms include, but are not limited to, syringes and needles, urethral suppositories, or transurethral implants, ampoules or vials, or transdermal vehicles or devices, such as creams, lotions or patches.

The active ingredient can also be delivered to the penile and cavernosal tissue transdermally. A suitable delivery vehicle or device is situated in direct contact with the skin of the penis to effect delivery of the agent to the penile and cavernosal tissue. The vehicle or device may include agents which enhance the transdermal absorption rate or agents which aid in the absorption of the pharmaceutical composition into the cavernosal tissue.

A particularly preferred transdermal device of the present invention is a patch. A patch is designed to adhere to or be brought into contact with the skin of the penis so that the pharmaceutical composition contained by the patch can be absorbed transdermally and into the penile and cavernosal tissue. The patch may also contain agents which enhance, control, or a combination of both, the transdermal absorption of the pharmaceutical composition and/or the absorption of the pharmaceutical composition into the penile and cavernosal tissue. Optionally, these agents can be applied in conjunction with the pharmaceutical composition, at a different time, and/or a different route of administration. The patch may also include adhesives specially designed to adhere to the often sensitive skin of the penis.

Kits comprising pharmaceutical compositions of the invention formulated in sterile unit dosage forms suitable for administration to the penile tissue, includes instructions for use in written, oral, videotape, compact disc, other digital electronic form, or other recorded media, are contemplated. Conveniently, a kit wherein the sterile unit dosage forms are for oil based depot injections and instructions for use is provided.

Usual systemic doses for testosterone may range from around 0.5 to 160 mg/day depending on the route of administration and the reason for treatment.

The appropriate dosage and frequency of treatment may vary depending upon desire or need of the degree of enhanced erectile function sought. Other health related factors would also be considered. Men without need of great enhancement of their erectile function may not need maximal treatment. The androgen dosage can be in the range of 0.01 to 100 mg/day, more preferably the dosage is in the range of 0.1 to 20 mg/day of testosterone, or equivalent dose of DHT or other androgen, androgen receptor agonist, or molecule which binds to an androgen receptor, depending on the route of administration.

The frequency of administration may be in the range of two to three times a day for intercavernosal injection, more preferably from 3 to 7 times a week, or as infrequently as monthly for delayed release formulations or topical administrations. The patient's condition should be monitored and the dosage adjusted, usually titrated upward, if enhanced erectile function is not achieved. Enhancement in erectile function may start immediately, but the major therapeutic effect may be expected to be achieved within 2 weeks to 6 months, more often within 4 weeks to 3 months. This may be followed by a maintenance phase during which there are intermittent or less frequent administrations. This may involve administrations of at least quarterly, bimonthly, biweekly, weekly injections, depending on the route of administration.

DETAILED DESCRIPTION OF PREFERRED EMBODIMENTS

In order that the invention may be better understood, preferred embodiments will now be described by way of example only with reference to the following Examples.

Example 1

Patient A

A 30 year old patient was using intracavernosal injections to effect an erectile response by routinely applying 1.5 ug of prostaglandin E1 intracavernosally to the penis. This treatment normally caused a partial erection (70-75% firmness) for about one hour.

It was found that administration by injection of 20 ug of LR3IGF-1 in addition to the prostaglandin E1 caused a dramatic increase in the firmness and duration of the patient's erectile response to effect a priapism, i.e. a 100% erection that did not soften with Pseudophed 180 mg and vigorous exercises. Patient also noted that immediately after 20 ug of LR3 IGF-1 taken alone without the prostaglandin E1 gave improved erectile function.

Example 2

Patient B

A 51 year old patient routinely applied 6 ug prostaglandin E1 intracavernosally to the penis. He was only able to obtain a partial erection (60% firmness) for about 30 mins as a result of venous leakage. Without medication he could not achieve a natural erection stronger than 50%.

The patient then started adding 3 ug LR3 IGF-1 to the 6 ug prostaglandin E1 and when injected the first time it caused an 80-90% erection lasting about 1 hour.

Over a two week period, the patient carried out several more injections of 3 ug of LR3 IGF-1 to his 6 ug of prostaglandin E1 and during this time reported that the firmness of his erections were up to 100% in firmness while the duration increased to up to 2 hours. In addition, the patient's erectile function increased during this period and he began getting firm spontaneous erections without the need for medications.

Patient B stopped using LR3 IGF-1 and within 2 weeks, he began to notice a gradual decline of erectile function. After two years the patient continued to episodically use LR3 IGF-1.

The patient continued to have good erections until he began to develop clinical hypothyroidism which ensued after several months of severe radicular neuralgic pain following an injury. As a result of chronic pain and clinical hypothyroidism, the patient's erectile dysfunction had declined and he was now not obtaining firm erections when even up to 6-10 mcg of LR3 IGF1 was being added to the PGE1 injections and PDE5's.

But when 10 mg of Testosterone was added to the IC mixture of 6 mcg of LR3 IGF1 plus 6 mcg of PGE1 the patient once again started to obtain dramatically harder and firmer erections. These injections were being used 2-3 times per week, and the patient began to experience a dramatic return of erectile function. After about a month the patient was able to have sexual intercourse without any medications.

Example 3

Patient C

Patient C was a 48 year old man who had been experiencing severe erectile dysfunction for over 5 years. Patient C originally was not having any erections even with maximal doses of Viagra®, Cialis® or Levitra®. He was also unable to obtain a usable erection even with maximum doses of PGE1 40 ug/ml plus a triple mix with papavarine, atropine and phentolamine.

Patient C was then given some 1% testosterone gel that he was to apply twice daily to his penis. After a few weeks on the topical testosterone the patient and was able to obtain some usable responses to 80-100 units of PGE1 40 ug/ml combined with a triple mix of papavarine, atropine and phentolamine. But even though he was now getting usable erections with high doses of intracavernosal injections, he still could not function with maximal doses of the PDE5: Viagra®, Cialis® and Levitra®. When using these oral agents with daily topical androgens the patient was still not able to achieve useable responses with these oral agents.

Finally when the patient began injecting 10 ug to 20 ug of IGF-1 or 6-10 ug of LR3 IGF1 sub-cutaneously plus applying the topical 1% testosterone gel into his penis at a frequency of 3-4 times per week for a period of one month his erections dramatically improved. This combination of IGF's plus androgens plus intracavernosal vasodilators resulted in a dramatic improvement in erectile function. Patient C was now getting firm erections with only 20-40 units of his intracavernosal meds, and he was now obtaining firm usable erections with the PDE5's on the days he did not use his intracavernosal medications combined with IGF's.

The patient continued to use IGF injections, but ran out of his topical testosterone, and after about two weeks without his topical agent, he began to find the PDE5's were no longer working.

The patient was then given some Deletestryl™ 200 mg/ml of testosterone and was mixing 7 units of testosterone with 10 ug of LR3IGF1. He was injecting this intracavernosally and immediately saw his erectile function improve again, such that he was once again able to get and sustain usable erections and perform successful intercourse.

Example 4

Patient D

A 62 year old man with long standing erectile dysfunction began seeing an anti-aging physician. His erectile dysfunction was not responding to the oral medications of Viagra®, Cialis®, or Levitra® and had been on intracavernosal injections for years.

He did not report a significant improvement in his erectile function since starting on Growth Hormone injections daily. After 1 year on Growth Hormones, he began to inject IGF1 subcutaneously in his abdomen at a dose of 50-100 ug/day.

While on systemic doses of 50-100 ug of IGF1 but prior to starting to add the IGF1 directly into the penis or to combine it with his intracavernosal injections, the patient was not getting adequate erections when using his intracavernosal meds. Before applying the IGF1 locally to the penis the patient found that even if he combined maximal oral doses of Viagra®, Cialis®, or Levitra® with his intracavernosal injections he was frequently going soft during intercourse.

After several months on the IFG1 injections into the abdominal area, he started to intermittently apply some of these daily injections of IGF1 into his penis. The patient immediately experienced improved erectile function and had to reduce the strength of his erectile dysfunction medications because the erections were lasting too long.

After about three months of intermittently applying some of his 50-100 ug daily IGF1 injections subcutaneously into the penis the patient stopped these subcutaneous injections into the penis and instead the patient began to also combine 5-10 ug of IGF1 with his intracavernosal injections and he reduced his daily dose of IGF1 to 50 ug injected into the abdomen. After starting the penile and intracavernosal injections of IGF1 locally into the penis the patient had to reduce his intracavernosal dose by over 50% because the erections were staying hard too long at his old dose and sometimes he would use oral medications instead of injections because he was now getting usable erections with Viagra® or Levitra® or Cialis® without the need for intracavernosal injections.

Finally this patient was diagnosed with low serum testosterone and he was started on topical 1% Testosterone gel. On starting this treatment he noticed an even better level of erectile function, so that his spontaneous and morning erections had become firmer and more frequent, and his erection with IC Meds and oral PDE5's had improved.

He was also now starting to get longer-lasting and firmer spontaneous erections even without any medications, and he also had to cut down the dose of his intracavernosal medicament since starting the local application of treatment to avoid getting priapisms.

Example 5

Patient E

An 81 year old patient was using intracavernosal injection for over 12 years. Initially, with maximal strength intracavernosal injections, the patient able to penetrate and maintain a usable erection. But his erectile function continued to decline and for the past couple of years he was unable to function. Even when he combined maximal strength intracavernosal injections with a ring his erections were less than 50%. This patient had no spontaneous erections and he had not had morning erects for over ten years.

The patient started applying 0.2 ml of 2.5% testosterone cream to the head and shaft of his penis twice daily and after a few months he was now getting 70-75% erections which were often going soft after penetration.

While continuing to apply the 0.2 ml of 2.5% testosterone cream to the head and shaft of his penis twice daily, the patient also received four subcutaneous injections of Hug of IGF1 into the shaft of his penis that were injected at intervals of seven days.

The combination of daily topical testosterone being applied to the penis and the four weekly applications of IGF1 injected directly into the penis dramatically improved the patient's erectile function such that he was now getting dramatically harder erections under all circumstances.

The application of these medications directly into the penis caused him to start getting regular morning erections and spontaneous erections. The patient could get firm erections with masturbation which had not happened for many years and his erections after an intracavernosal injection were now lasting over 40 minutes at over 80% hardness. These improvements persisted for several weeks after the last IGF1 injection and the fact that these improvements continued long after the medication had been cleared from the body clearly demonstrates that they had induced actual long standing physical changes in the patient's penis.

Example 6

Patient F

A 37 year old patient with erectile dysfunction was using Cialis on a prn basis to treat his erectile dysfunction. The patient applied 2 ug of lr3 IGF1 subcutaneously to his penis three times per week for one month.

By the second local application of lr3 IGF1 into the patient's penis, he began experiencing firmer spontaneous erections and by the third week he was no longer dependant on Cialis.

When seen three months after stopping the lr3 IGF1 injections the patient was continuing to be sexually active without Cialis. These improvements in erectile function persisted for several weeks after the last IGF1 injection. The fact that these improvements continued long after the lr3 IGF1 had been cleared from the body clearly demonstrates that it had induced long standing physical changes in the patient's penis.

Example 7

Patient G

This 55 year old male patient had been having erectile dysfunction for over three years. He was not able function sexually with Viagra, Levitra or Cialis. He had never used intracavernosal injections to treat his erectile dysfunction.

In an attempt to improve his erectile function the patient had been applying 0.2 grams of 2% Dihydrotestosterone cream to his penis for over six months with only a slight improvement. With the 0.2 grams of 2% Dihydrotestosterone cream his spontaneous erections with his wife were getting harder initially but once he penetrated his erections were still going soft well before he could achieve an orgasm.

The patient then received twice weekly subcutaneous injections of 25 ug of IGF1 into the shaft of his penis. The patient immediately began experiencing firmer spontaneous erections and was now easily getting and sustaining firm erections through to orgasm and ejaculation. When seen over several months the patient improvements in erectile function would persist for several weeks after the last IGF1 injection. But the patient was needing to inject 25 ug of IGF1 into the shaft of his penis once or twice per month to maintain optimal erections.

The fact that these improvements continued weeks after the IGF1 had been cleared from the penis and the body clearly demonstrates that Dihydrotestosterone and IGF1 had induced long standing physical changes in the patient's penis.

Although this disclosure has described and illustrated certain preferred embodiments of the invention, it is to be understood that the invention is not restricted to those particular embodiments. Rather, the invention includes all embodiments which are functional or mechanical equivalence of the specific embodiments and features that have been described and illustrated.

The embodiments of the invention in which an exclusive property or privilege is claimed are defined as follows:

1. A method of enhancing male erectile function in a male having erectile dysfunction comprising administering to said male a composition comprising:
    an erectile function-enhancing amount of an insulin-like growth factor selected from the group consisting of IGF-1 (Somatomedin-C) and analogue LR3 IGF1; and
    an androgen, in admixture with pharmaceutically acceptable diluents or carriers, wherein said composition is locally administered to the penis by injection or transdermal application and wherein the insulin-like growth factor is administered in the amount of 2-5 µg daily.

2. The method of claim 1 wherein said insulin-like growth factor is IGF-1.

3. The method of claim 1 wherein said insulin-like growth factor is LR3 IGF1.

4. The method of claim 1 wherein the transdermal application is in the form of patches, creams or lotions.

5. A method of enhancing male erectile function in a male having erectile dysfunction comprising administering to said male a composition comprising:
    an erectile function-enhancing amount of an insulin-like growth factor selected from the group consisting of IGF-1 (Somatomedin-C) and analogue LR3 IGF1; and
    an androgen, in admixture with pharmaceutically acceptable diluents or carriers, wherein said composition is locally administered to the penis by injection or transdermal application and wherein the insulin-like growth factor is administered in the amount of 40-80 µg/kg, twice daily, up to a maximum of 120 µg/kg, twice daily.

6. The method of claim 5 wherein said insulin-like growth factor is IGF-1.

7. The method of claim 5 wherein said insulin-like growth factor is LR3 IGF1.

8. The method of claim 5 wherein the transdermal application is in the form of patches, creams or lotions.

* * * * *